United States Patent [19]

Kase et al.

[11] Patent Number: 5,296,635

[45] Date of Patent: Mar. 22, 1994

[54] PREPARATION OF BIS(3-NITROPHENOXY) COMPOUND

[75] Inventors: Motohiro Kase; Hitoshi Nakayama; Masaru Wada; Teruyuki Nagata, all of Fukuoka; Akihiro Yamaguchi, Kanagawa, all of Japan

[73] Assignee: Mitsui Toatsu Chemicals, Inc., Tokyo, Japan

[21] Appl. No.: 975,952

[22] Filed: Nov. 13, 1992

Related U.S. Application Data

[63] Continuation of Ser. No. 631,493, Dec. 21, 1990, abandoned.

[30] Foreign Application Priority Data

Dec. 28, 1989 [JP] Japan .................. 1-338210
Dec. 28, 1989 [JP] Japan .................. 1-338211

[51] Int. Cl.$^5$ .............. C07C 315/04; C07C 319/20; C07C 205/06; C07C 41/09
[52] U.S. Cl. ........................ 568/30; 568/36; 568/44; 568/306; 568/586
[58] Field of Search ............ 568/585, 586, 30, 36, 568/44, 306

[56] References Cited

FOREIGN PATENT DOCUMENTS

| | | | |
|---|---|---|---|
| 679318 | 9/1966 | Belgium | 568/586 |
| 192480 | 8/1986 | European Pat. Off. | |
| 193358 | 9/1986 | European Pat. Off. | |
| 61-194050 | 8/1986 | Japan | |
| 1-190652 | 7/1989 | Japan | 568/586 |

OTHER PUBLICATIONS

Weissberger, *Physical Methods of Organic Chemistry*, pp. 658–661, 1959.

*Primary Examiner*—Marianne M. Cintins
*Assistant Examiner*—Margaret J. Page
*Attorney, Agent, or Firm*—Burns, Doane, Swecker & Mathis

[57] ABSTRACT

A preparation process of a bis(3-nitrophenoxy) compound represented by the formula:

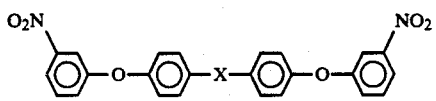

wherein X is a direct bond, divalent hydrocarbon having from 1 to 10 carbon atoms or a divalent group selected from $-C(CF_3)_2$, $-CO-$, $-S-$, $-SO-$, $-SO_2-$ or $-O-$, which comprises reacting 4,4'-bisphenol with m-dinitrobenzene in the presence of an alkali metal carbonate or alkali metal hydrogen carbonate having a particle size of 250 μm or less while removing generated water from the reaction system during the reaction. In one embodiment of the process, the reaction is carried out while simultaneously adding 4,4'-bisphenol and m-dinitrobenzene to a reaction vessel which was previously charged with the base and an aprotic polar solvent.

2 Claims, No Drawings

PREPARATION OF BIS(3-NITROPHENOXY) COMPOUND

This application is a continuation of application Ser. No. 07/631,493, filed Dec. 21, 1990 now abandoned.

BACKGROUND OF THE INVENTION

1. Field of the Invention

The present invention relates to an improved process for preparing a bis(3-nitrophenoxy) compound represented by the formula (II):

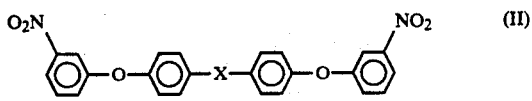

wherein X is a direct bond, divalent hydrocarbon having from 1 to 10 carbon atoms or a divalent group selected from $-C(CF_3)_2-$, $-CO-$, $-S-$, $-SO-$, $-SO_2-$ and $-O-$.

The bis(3-nitrophenoxy) compund is an important compound used as a material for preparing a monomer which is in turn used in the preparation of heat resistant high molecular weight polymers, polyamides and polyimides in particular. For example, ether diamine obtained by reducing the compound can be used as a diamine component of polyimide which can provide adhesive having excellent heat resistance.

2. Description of the Related Art

A process for the condensation of 4,4'-bisphenols represented by the formula (I):

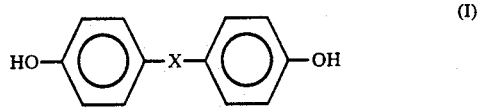

wherein X is a direct bond, divalent hydrocarbon having from 1 to 10 carbon atoms or a divalent group selected from $-C(CF_3)_2-$, $-CO-$, $-S-$, $-SO-$, $-SO_2-$ and $-O-$, with m-dinitrobenzene to prepare a bis(3-nitrophenoxy) compound represented by the formula (II):

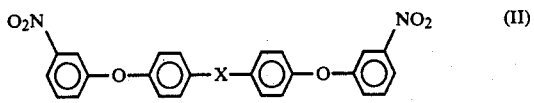

wherein X is the same as in the formula (I), has already been known in Japanese Laid-Open Patent SHO 61-194050(1986) and 62-45563(1987).

According to Japanese Laid-Open Patent SHO 61-194050, the condensation reaction can be carried out in an aprotic polar solvent in the presence of a base.

According to Japanese Laid-Open Patent SHO 62-45563, the condensation reaction can be further accelerated by using a phase transfer catalyst under the same conditions.

These processes can provide the desired bis(3-nitrophenoxy) compound without using an expensive reaction accelerator such as crown ethers. These processes, however, have the following problems.

(1) Alkali metal carbonate on alkali metal hydrogen carbonate used as a base is required in an excessive amount such as 2.0 to 2.6 moles per mole of 4,4'-bisphenol and hence is disadvantageous in industry.

(2) When the reaction is carried out according to these processes, reproducibility of the reaction is poor and consistent results cannot be obtained even though the reaction is conducted under the same conditions. Consequently, the products cannot maintain consistent quality.

(3) The reaction cannot be completed unless m-dinitrobenzene is used in an amount of from 2.3 to 2.6 moles per mole of the bisphenol. When the reaction is conducted by using a smaller amount, bisphenol is reacted with only one mole of m dinitrobenzene and the resultant mononitrophenoxy compound remains in a large amount after finishing the reaction which causes a reduction in the yield.

(4) Excess m-dinitrobenzene causes decomposition by itself or partly leads to decomposition after reacting with the bisphenol to form tarry materials or 3,3'-dinitroazobenzene, or partly remains unreacted. The desired bis(3-nitrophenoxy) compound can be separated from these by-products with relative ease and is obtained in a good purity. However, in the distillation for recovering the solvent containing these impurities unreacted m-dinitrobenzene and tarry materials derived from dinitrobenzene are concentrated at the bottom of the distillation vessel and hence lead to a danger of explosion. Consequently, efficient recycle of the reaction solvent cannot be performed, which is disadvantageous in industry.

SUMMARY OF THE INVENTION

One object of the present invention is to provide an improved process for the preparation of a bis(3-nitrophenoxy) compound, with a high purity and without a decrease in the yield and consistently as compared with already known processes.

Another object of the present invention is to decrease the amount of an alkali metal carbonate or alkali metal hydrogen carbonate used as a base without lowering the yield and purity of the bis(3-nitrophenoxy) compound.

A further object of the present invention is to lower the proportion of m-dinitrobenzene to 4,4'-bisphenol without decreasing the purity and yield of the bis(3-nitrophenoxy) compound and to enable the recovery of the aprotic polar solvent used in the reaction.

As a result of an intensive investigation in order to accomplish these objects, the present inventors have found the following facts in the condensation reaction of 4,4'-bisphenol and m-dinitrobenzene. That is, the amount of the base used can be reduced to 2.0 to 3.0 mole equivalent per mole of bisphenols and the desired bis(3-nitrophenoxy) compound can be favorably and consistently prepared by using as the base, alkali metal carbonate or alkali metal hydrogen carbonate having a particle size of 250 μm or less and by conducting the reaction while removing generated water from the reaction system during the reaction.

They have further found that the m-dinitrobenzene used can be reduced to a minimum amount and the desired bis(3-nitrophenoxy) compound can be obtained in good yield and high purity by previously charging the base and the aprotic polar solvent in a reaction vessel and by conducting the reaction with simultaneous addition of the 4,4'-bisphenol and m-dinitrobenzene. Thus the present invention has been completed.

That is, one aspect of the present invention is a process for the preparation of a bis(3-nitrophenoxy) compound by conducting a condensation reaction of a 4,4'-bisphenol represented by the formula (I):

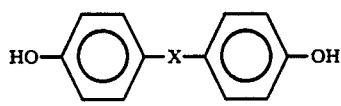 (I)

wherein X is a direct bond, divalent hydrocarbon having from 1 to 10 carbon atoms or a divalent group selected from —C(CF$_3$)$_2$—, —CO—, —S—, —SO—, —SO$_2$— and —O, with m-dinitrobenzene in the presence of a base in an aprotic polar solvent to prepare the bis(3-nitrophenoxy) compound represented by the formula (II):

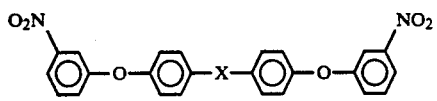 (II)

wherein X is the same as in formula ( ), comprising conducting the reaction by using an alkali metal carbonate or alkali metal hydrogen carbonate having a particle size of 250 μm or less as a base while removing generated water from the reaction system during the reaction; and said process for the preparation of the compound comprising adding the 4,4'-bisphenol and m-dinitrobenzene at the same time as raw materials.

The above improved process of the present invention can lower the amount of alkali metal carbonate or alkali metal hydrogen carbonate used as the base to 2.0 to 3.0 mole equivalent and also decrease the amount of m-dinitrobenzene to 2.0 to 2.1 moles per mole of 4,4'-bisphenol. The desired bis(3-nitrophenoxy) compound can be prepared in good yield, in high purity and with excellent reproducibility. Also in the distillation recovery step of the reaction solvent, solvent recycle can be carried out safely and in good efficiency. Consequently, the process of the invention is very valuable in industry.

DESCRIPTION OF THE PREFERRED EMBODIMENTS

The raw materials used in the present invention are m-dinitrobenzene and 4,4'-bisphenol represented by the above formula Exemplary 4,4'-bisphenols which can be used include 4,4'-dihydroxybiphenyl, 4,4'-dihydroxydiphenylmethane, 2,2-bis(4-hydroxyphenyl)propane, 2,4 bis(4-hydroxyphenyl)-2-methylpentane, 2,4-bis(4-hydroxyphenyl)-4-methyl-1-pentene, 2,2-bis(4-hydroxyphenyl)-hexafluoropropane, 4,4'-dihydroxybenzophenone, 4,4'-dihydroxydiphenyl sulfide, 4,4'-dihydroxydiphenyl sulfoxide, 4,4'-dihydroxydiphenyl sulfone and 4,4'-dihydroxydiphenyl ether.

The amount of m-dinitrobenzene is from 2.0 to 2.6 moles per mole of the bisphenol. In the case of simultaneously adding bisphenol and m-dinitrobenzene in particular, it is preferred to use from 2.0 to 2.1 moles. Use of m-dinitrobenzene exceeding 2.6 moles is not advantageous in industry. On the other hand, when m-dinitrobenzene is used in an amount of less than 2.0 moles, the amount of m-dinitrobenzene is insufficient and a mononitrophenoxy derivative remains after reaction to decrease the yield of the desired product.

The base used in the invention is an alkali metal carbonate or an alkali metal hydrogen carbonate and includes, for example, calcium carbonate, sodium carbonate, lithium carbonate, potassium hydrogen carbonate and sodium hydrogen carbonate. Preferred bases are potassium carbonate and potassium hydrogen carbonate. The base can be used singly or as a mixture.

The amount of the base used is in the range of from 2.0 to 10 mole equivalent per mole of the raw material bisphenol. Satisfactory effects can be obtained within the range.

Commonly marketed alkali metal carbonates or alkali metal hydrogen carbonates contain various sizes of particles. In the process of the present invention, it is extremely important to use an alkali metal carbonate or alkali metal hydrogen carbonate having a specific range of particle size. Particle size distribution may be permitted. It is, however, desired to contain the smallest amount of the particle having a size of more than 250 μm. Under the reaction conditions of the invention, most of the alkali metal carbonate or alkali metal hydrogen carbonate is not dissolved in the solvent and exist in a suspended state. Consequently, a particle size exceeding 250μm lowers the dissolution rate of the particle into the reaction system and unfavorably decreases the overall rate of the condensation reaction. When a large sized particle is contained in a particle size distribution, for example, when a commercial base is used as such, a satisfactory reaction rate cannot be obtained unless the amount of the base is increased. It is accordingly required to use an excess amount of the base, and additionally the particle size varies widely. As a result, reproducibility of the reaction is poor.

In the process of the invention, the alkali metal carbonate or alkali metal hydrogen carbonate used has a particle size of 250 μm or less, and the reaction is carried out while removing generated water from the reaction system during the reaction. Thus the amount of the base used can be decreased and the desired bis(3-nitrophenoxy) compound can be obtained in an increased yield and with excellent reproducibility.

The amount of the base used is in the range of from 2.0 to 3.0 mole equivalent per mole of the raw material bisphenol. In order to neutralize nitrous acid ions formed in the condensation reaction, an equivalent amount or more of the base is required. It is, however, satisfactory to use 3.0 mole equivalent.

The process of the present invention may use as a reaction accelerator an ether containing chain alkylamine as disclosed in Japanese Laid-Open Patent SHO 62-45563(1987), quaternary ammonium salt, quaternary phosphoric acid salt, large ring polyether such as a crown ether, nitrogen containing large ring polyether such as crypltate, nitrogen containing chain polyether, phase transfer catalyst such as polyethylene glycol and its alkyl ether, copper powder and copper salt.

The aprotic polar solvent which can be used for the reaction includes, for example, N methylformamide, N,N-dimethylformamide, N,N-dimethylacetamide, dimethyl sulfoxide, dimethyl sulfone, sulfolane, 1-methyl-2 pyrolidinone, 1,3-dimethyl-2-imidazolidinone, N,N,N',N'-tetramethylurea, hexamethylphosphotriamide and 1,3-dimethyl-3,4,5,6-tetrahydro-2(1H)-pyrimidine. No particular limitation is imposed on the total amount of the aprotic polar solvent. The satisfactory total amount is usually from 1 to 10 times the total weight of the raw materials used.

In the practice of the present invention, no particular restriction is placed upon the charging method of the raw materials. For example, the following methods can be carried out.

(1) A prescribed amount of bisphenol, m-dinitrobenzene, the base and the solvent are charged at one time and the resulting mixture is reacted.

(2) A prescribed amount of the base, solvent and a portion of the raw materials are previously charged to form a reaction system and the reaction is carried out while adding the remainder of the raw materials.

(3) A prescribed amount of the base and the solvent are previously charged and the reaction is carried out while adding the total amount of the raw materials.

(4) A particularly preferred embodiment is a method for previously charging the base and the solvent and then adding the raw materials, i.e., bisphenol and m-dinitrobenzene at the same time.

The particularly preferred embodiment will hereinafter be illustrated in detail.

m-Dinitrobenzene has poor thermal stability under basic conditions and leads to unfavorable side reactions such as the generation of tarry materials due to decomposition and formation of 3,3'-dinitroazoxybenzene by condensation of two molecules.

These side reactions must be inhibited in order to reduce the amount of m-dinitrobenzene used and to prepare the desired bis(3-nitrophenoxy) compound in an increased yield and in higher purity.

Use of the base is inevitable in the reaction of the invention. In the case of inhibiting the side reactions and enhancing selectivity of the condensation reaction, if the reaction rate of the side reactions has kinetically hi9her dependence upon the concentration of m-dinitrobenzene as compared with the reaction rate of the condensation reaction, the object should be accomplished by extremely decreasing the concentration of m-dinitrobenzene which is present in the system during the reaction. An exemplary method is to add m-dinitrobenzene to a solvent containing the prescribed amount of bisphenol and the base as disclosed in Japanese Laid-Open Patent SHO 61-194050(1986).

The method, however, decreases yield as compared with the reaction conducted by simultaneous addition of the raw materials. The reason for the reverse result is that the mononitrophenoxy derivative obtained by reacting the bisphenol with only one mole of m-dinitrobenzene is unstable under the reaction conditions of the invention. Consequently, in order to decrease the amount of m-dinitrobenzene used and also to prepare the bis(3-nitrophenoxy) compound in a good yield and high purity, side reactions of both m-dinitrobenzene and the mononitrophenoxy derivative must be simultaneously inhibited.

In the process of the invention, the base and the aprotic polar solvent are previously charged into a reaction vessel and then the reaction is carried out while simultaneously adding the 4,4'-bisphenol and m-dinitrobenzene, whereby the side-reactions are inhibited and the desired bis(3-nitrophenoxy) compound are prepared in good yield and high purity.

In the process, both raw materials of the condensation are gradually added into the system during the reaction and immediately reacted with each other without accumulation in the system.

In the embodiment, the amount of m-dinitrobenzene is in the range of from 2.0 to 2.1 moles per mole of bisphenols when both materials are simultaneously added to the reaction system, so that an excess of the bisphenol in the reaction system does not occur during the reaction. Hence the reaction can progress without accumulation of the mono nitrophenoxy derivative as compared with the above mentioned method of adding m-dinitrobenzene alone.

According to the process, the reaction can be carried out while maintaining both m-dinitrobenzene and bisphenols at low concentrations during the reaction. Thus the process can inhibit any unfavorable side reactions such as decomposition and azoxylation of m-dinitrobenzene and decomposition of the mononitrophenoxy derivative. As a result, m-dinitrobenzene used in the process can be reduced to a minimum amount as compared with conventional processes and the desired bis(3-nitrophenoxy) compound can be prepared in good yield and high purity.

No particular restriction is imposed on the embodiment for the addition of the raw materials. For example, the m-dinitrobenzene and bisphenol are dissolved in a portion of the solvent for use in the reaction and the resulting solution can be added with relative ease in view of operation.

Each raw material is separately dissolved in the solvent and the resultant two kinds of solution may be respectively added dropwise. It is however, desirable to add dropwise in the form of a one component type raw material solution which is a uniform solution of both materials.

The mole ratio of m-dinitrobenzene added per unit time is preferably in the range of from 2.00 to 2.06 moles per mole of bisphenols. When the mole ratio of m-dinitrobenzene added is higher than the range, m-dinitrobenzene is present in excess and accumulates in the reaction system. On the other hand, a mole ratio lower than this range leads to shortage of m-dinitrobenzene and the mononitrophenoxy derivative accumulates in the reaction system to cause a decrease in the yield.

In the process of the invention, the addition mole ratio per unit time of m-dinitrobenzene to the bisphenol must be maintained within the above narrow range. It is thus preferable to add in the form of the one component type raw material solution obtained by uniformly dissolving both materials.

When these materials are separately added, respective rates of addition must be simultaneously controlled, which control is relatively difficult. However, in the case of using one component type raw material solution obtained by uniformly dissolving both materials, the mole ratio of the raw materials per unit time can be maintained during addition in the range of from 1:2.0 to 1:2.1, which range is equal to or very close to the theoretical mole ratio of the bisphenol to m-dinitrobenzene. Thus addition operation can be controlled with ease, carried out with one apparatus and is advantageous in view of equipment.

No particular limitation is imposed on the amount of the solvent in preparing the raw materials solution as long as both condensation materials are completely dissolved and no crystals precipitate during dropwise addition.

The condensation reaction of the invention is carried out while removing the generated water from the reaction system by using a small amount of an azeotropic solvent such as benzene, toluene, xylene or monochlorobenzene, by blowing an inert gas such as nitrogen gas or argon gas, or by combination of both procedures.

Water remaining in the system inhibits the condensation reaction, slows down reaction velocity, causes accumulation of the raw material m dinitrobenzene and intermediate mononitrophenoxy derivative, and leads to a decrease in the yield.

The amount of the azeotropic solvent may be in a small amount and is usually from 2 to 5% of the total amount of the aprotic polar solvent used for the reaction. In the case of using the azeotropic solvent, packing is filled in the passageway to the reflux condenser fitted with a water separator, a vapor mixture of water, azeotropic solvent and reaction solvent is introduced into the passageway, and a rectification/separation effect of water and the azeotropic solvent from the aprotic polar solvent is desirably enhanced by causing a reflux in the passageway.

The aprotic polar solvent used for the reaction solvent usually has high affinity for water and the above azeotropic solvent. When the aprotic polar solvent arrives in the reflux condenser together with generated water and the azeotropic solvent, the aprotic polar solvent partitions itself between the water which is removed in the separator and the azeotropic solvent which flows back to the reaction system.

When the aprotic solvent is present in the azeotropic solvent, the water which is to be removed has increased solubility in the azeotropic solvent and a larger amount of the water circulates to the reaction system accompanied by the azeotropic solvent. Thus the effect for removing the generated water is decreased which gives adverse effects on the reaction.

The reaction of the invention can be carried out under atmospheric pressure. In order to enhance the reaction rate, the reaction can also be conducted at a temperature above the boiling point of the solvents or under increased pressure.

The reaction temperature is in the range of usually from 100° to 240° C., preferably from 140° to 180° C. A reaction temperature lower than 100° C. leads to a very slow rate of reaction or no reaction at all. On the other hand, reaction conditions exceeding 240° C. accelerate formation of tarry materials from the raw materials, intermediate and reaction product and thus decrease the yield. A reaction temperature in the range of from 180° to 240° C. is suitable for increasing the reaction rate. However, in the case where the boiling point of the reaction solvent is in the above temperature range, the reaction must be conducted under increased pressure and requires excessive equipment which circumstances are not so advantageous in industry.

The rate of adding the raw materials into the reaction system must be equal to the reaction rate. When the addition rate is too high, the added raw materials do not react, accumulate in the reaction system, and lead to a decrease in the yield. On the other hand, too low a rate of addition causes accumulation of the intermediate mononitrophenoxy derivative in the reaction system for a long time and results in a decrease in the yield. The optimum addition rate varies depending upon the reactivity of the raw material bisphenol. For example, 4,4'-dihydroxybiphenyl is preferably added in such a rate that the whole amount is added over 3 to 6 hours.

The commonly preferred embodiments for practicing the process of the present invention is, for example, as follows.

To a reaction vessel equipped with a reflux condenser connected with the reaction vessel through a packed column and fitted with a separator, a thermometer, a dropping device and a stirrer, prescribed amount of m dinitrobenzene and 4,4'-bisphenol, 250 μm (60 mesh) minus sieve portion of alkali metal carbonate or alkali metal hydrogen carbonate, aprotic polar solvent and a small amount of an azeotropic solvent are charged. The reaction vessel is then heated with stirring to a prescribed temperature to carry out the reaction. The generated water during the reaction is distilled off with the azeotropic solvent, condensed in the reflux condenser, and separated in the separator. Stirring is continued at the prescribed temperature until residual mononitrophenoxy compound and m-dinitrobenzene are completely reacted and the desired bis(3-nitrophenoxy) compound is formed.

In the case of adding both raw materials 4,4'-bisphenol and m-dinitrobenzene at the same time, a reaction vessel equipped with a reflux condenser connected with the reaction vessel through a packed column and fitted with a separator, a thermometer, a dropping device and a stirrer, is charged with the base mentioned above, the aprotic polar solvent and a small amount of the azeotropic solvent. A solution of the aprotic polar solvent containing prescribed amounts of m-dinitrobenzene and 4,4'-bisphenol is charged to the dropping device.

The reaction vessel is heated with stirring to the prescribed temperature and the solution in the dropping device is added dropwise to the reaction vessel over a prescribed period of time. After finishing dropwise addition, stirring is continued at the prescribed temperature until residual mononitrophenoxy derivative and m-dinitrobenzene are completely reacted and the desired bis(3-nitrophenoxy) compound is formed.

Completion of the reaction is confirmed by thin layer chromatography or high performance liquid chromatography, and then inorganic salts such as potassium nitrite are filtered off from the reaction mixture. Water is poured in to the filtrate and precipitated crystal is filtered to obtain the desired bis(3-nitrophenoxy) compound. The crude product has a considerably high purity as such and can also be highly purified by recrystallization or activated carbon treatment.

Exemplary bis(3-nitrophenoxy) compounds which can be prepared by the process of the invention include 4,4'-bis(3-nitrophenoxy)-biphenyl,
4,4'-bis(3-nitrophenoxy)diphenylmethane,
2,2-bis [4-(3-nitrophenoxy)phenyl]propane,
2,4-bis [4-(3-nitrophenoxy)phenyl]-2-methylpentane,
2,4-bis [4-(3-nitrophenoxy)phenyl]-4-methyl-1-pentene,
2,2-bis [4 (3-nitrophenoxy)phenyl]hexafluoropropane,
4,4'-bis(3-nitrophenoxy)benzophenone,
4,4'-bis(3-nitrophenoxy)diphenyl sulfide,
4,4'-bis(3-nitrophenoxy)diphenyl sulfoxide,
4,4'-bis(3-nitrophenoxy)diphenyl sulfone and
4,4'-bis(3-nitrophenoxy)diphenyl ether.

The present invention will hereinafter be illustrated in detail by way of examples and comparative examples.

EXAMPLE 1

To a 2l reaction vessel equipped with a reflux condenser connected with the reaction vessel through a packed column and fitted with a separator, a thermometer, a dropping device and a stirrer, 277.4 g (1.65 mole) of m-dinitrobenzene (hereinafter referred to as DNB) and 139.7 g (0.75 mole) of 4,4'-dihydroxybiphenyl(hereinafter referred to as BIP), 134.8 g (0.975 mole) of 60 mesh (250μm) minus sieve potassium carbonate, 1496 g of N,N-dimethylformamide (hereinafter referred to as DMF) and 22 g of toluene were charged. The mixture in the reaction vessel was maintained at 150° to 154° C.

and stirred for 5 hours. Generated water was azeotropically distilled with toluene, condensed in the reflux condenser and separated in the separator.

The reaction mixture was cooled to 60° C. Solid matter in the reaction mixture was filtered and washed with 100 g of DMF and 100 g of toluene. Filtrate and washings were charged to a 3l crystallization vessel equipped with a stirrer and maintained at 90° C. To the resultant mixture in the vessel, 420 g of water was added dropwise with stirring over an hour and cooled to 30° C. The precipitated crystals were filtered to obtain 313.4 g of 4,4'-bis(3-nitrophenoxy)biphenyl. The crystals obtained had a purity of 96.1%. Yield after purity conversion was 93.7%.

COMPARATIVE EXAMPLES 1-4

In Comparative Example 1, 269.5 g of unsieved potassium carbonate was used, toluene was omitted, and the whole evaporated vapors were refluxed(a trace test of Japanese Laid-Open Patent SHO 61 194050).

In Comparative Example 2, 134.8 g of unsieved potassium carbonate was used.

In Comparative Example 3, 60 mesh plus sieve potassium carbonate was used.

In Comparative Example 4, 134.8 g of unsieved potassium carbonate was used, toluene was omitted, and all of the evaporated vapors were refluxed.

Other procedures carried out on the reaction and posts treatment were the same as described in Example 1.

Results are illustrated in Table 1.

EXAMPLES 2-6

The same procedures as described in Example 1 were carried out except that 4,4'-dihydroxybiphenyl was replaced with 171.2 g (0.75 mole) Of 2,2-bis(4-hydroxyphenyl)propane in Example 2, 204.3 g (0.75 mole) of 2,4 bis(4-hydroxyphenyl)-2-methylpentane in Example 3, 252.2 g (0.75 mole) of 2,2 bis(4-hydroxyphenyl)-hexafluoropropane in Example 4, 160.7 g (0.75 mole) of 4,4'-dihydroxybenzophenone in Example 5, and 187.7 g (0.75 mole) of 4,4'-dihydroxydiphenyl sulfone in Example 6. Results are illustrated in Table 2.

TABLE 1

| | Potassium carbonate | | Toluene azeotropic distillation | Reaction product | |
|---|---|---|---|---|---|
| | Amount (mole/BIP) | Sieve | | Yield (mole/BIP) | Purity (wt %) |
| Ex. 1 | 1.3 | minus sieve | yes | 93.7 | 96.1 |
| Comp. Ex. 1 | 2.6 | unsieved | no | 90.5 | 91.0 |
| Comp. Ex. 2 | 1.3 | ↑ | ↑ | 91.0 | 92.8 |
| Comp. Ex. 3 | 1.3 | plus sieve | ↑ | 77.3 | 81.5 |
| Comp. Ex. 4 | 1.3 | unsieved | ↑ | 85.9 | 87.6 |

TABLE 2

| | Bis(3-nitrophenoxy) compound | |
|---|---|---|
| | Yield (purity converted) (mole %/bisphenols) | Product purity (wt %) |
| Example 2 | 90.0 | 94.8 |
| Example 3 | 78.1 | 92.4 |
| Example 4 | 86.6 | 94.0 |
| Example 5 | 92.0 | 95.8 |

TABLE 2-continued

| | Bis(3-nitrophenoxy) compound | |
|---|---|---|
| | Yield (purity converted) (mole %/bisphenols) | Product purity (wt %) |
| Example 6 | 91.4 | 93.2 |

EXAMPLE 7

To the same reaction vessel as described in Example 1, 124.4 g (0.9 mole) of 60 mesh (250 μm) minus sieve potassium carbonate, 600 g DMF and 22 g of toluene were charged. A solution obtained by dissolving 256.0 g (1.523 mole) of DNB and 139.7 g (0.75 mole) of BIP in 300 g of DMF was charged to the dropping device.

The reaction vessel was heated to 150° C. with stirring and the solution in the dropping device was added dropwise at 150° to 154° C. over 6 hours. After finishing the addition, the reaction mixture was stirred for 2 hours at the same temperature. Generated water during the reaction was azeotropically distilled off with toluene, condensed in the condenser and separated in the separator.

The reaction mixture was cooled to 60° C. Solid matter in the reaction mixture was filtered and washed with 100 g of DMF and 100 g of toluene. Filtrate and washings were charged to a 3 l crystallization vessel equipped with a stirrer and maintained at 90° C. To the resultant mixture in the vessel, 420 g of water was added drop-wise with stirring over an hour and cooled to 30° C. The precipitated crystals were filtered to obtain 323.7 g of 4,4'-bis(3-nitrophenoxy)biphenyl. The crystals obtained had a purity of 99.1%. Yield after purity conversion was 99.8%. DMF was recovered by distillation from crystallization mother liquor) with a recovery of 97.5%.

COMPARATIVE EXAMPLES 5-9

The same reaction procedures as described in Example 7 were carried out by using a 1 l reaction vessel equipped with a reflux condenser connected with the reaction vessel through a packed column and fitted with a separator, a thermometer, a stirrer and a dropping device, if necessary. Raw materials used were 35.9 g (0.26 mole) of 60 mesh(250 μm) minus sieve potassium carbonate, 400 g of the whole amount of DMF 20 g of toluene, from 74.0 g (0.44 mole) to 68.1g(0.405 mole) of DNB, and 37.2 g (0.2 mole) of BIP.

In Comparative Example 5, 74.0 g of DNB was used and a solution obtained by dissolving BIP in 60 g of DMF was added dropwise.

In Comparative Example 6, the same reaction procedures were carried out as described in Comparative Example 5 except that 68.1 g of DNB was used.

In Comparative Example 7, 74.0 g of DNB was used and all of the raw materials were charged at one time.

In Comparative Example 8, the same reaction procedures as described in Comparative Example 7 were carried out except that 68.1 g of DNB was used.

In Comparative Example 9, the same reaction procedures as described in Example 7 were carried out except that a solution obtained by dissolving 74.0 g of DNB in 60 g of DMF was added dropwise.

COMPARATIVE EXAMPLE 10

The same reaction procedures as described in Example 7 were carried out except that amount of DNB was changed to 246 g.

In any of the Comparative Examples 5–10, the same post treatment procedures as described in Example 7 were carried out. Results of Example 7 and Comparative Examples 5–10 are illustrated in Table 3.

TABLE 3

4,4'-Bis(3-nitrophenoxy)biphenyl

| | Reaction procedure | DNB (mole/BIP) | Yield (mol %/BIP) |
|---|---|---|---|
| Ex. 7 | Both materials dropwise addition | 2.03 | 99.8 |
| Comp. Ex. 5 | BIP dropwise addition | 2.2 | 94.0 |
| Comp. Ex. 6 | ↑ | 2.025 | 89.3 |
| Comp. Ex. 7 | All materials charged at one time | 2.2 | 92.2 |
| Comp. Ex. 8 | ↑ | 2.025 | 87.4 |
| Comp. Ex. 9 | DNB dropwise addition | 2.2 | 87.9 |
| Comp. Ex. 10 | Both materials dropwise addition | 1.95 | 85.9 |

EXAMPLES 8–12

In the procedures of Example 7, 400 g of the solvent was charged to the reaction and 500 g of the solvent was used for dissolving the raw materials. 4,4'-Bisphenols used were 171.2 g(0.75 mole) of 2,2-bis(4-hydroxyphenyl)propane in Example 8, 204.3 g (0.75 mole) of 2,4-bis(4-hydroxyphenyl)-2-methylpentane in Example 9, 252.2 g (0.75 mole) of 2,2-bis(4-hydroxyphenyl)hexafluoropropane in Example 10, 160.7 g (0.75 mole) of 4,4'-dihydroxybenzophenone in Example 11, and 187.7 g (0.75 mole) of 4,4'-dihydroxydiphenyl sulfone in Example 12. The time for dropwise addition of the raw material solution was 9 hours in Example 8, 11 hours in Example 9, 8 hours in Example 10, 7 hours in Example 11, and 5 hours in Example 12. Other procedures conducted were the same as described in Example 7.

The results are illustrated in Table 4.

TABLE 4

| | Bis(3-nitrophenoxy) compound | |
|---|---|---|
| | Yield (purity converted) (mole %/bisphenol) | Product purity (wt %) |
| Example 8 | 96.8 | 99.0 |
| Example 9 | 82.1 | 94.7 |
| Example 10 | 91.0 | 97.6 |
| Example 11 | 99.0 | 99.8 |
| Example 12 | 96.4 | 98.2 |

What is claimed is:

1. A process for the preparation of a compound of the formula (II)

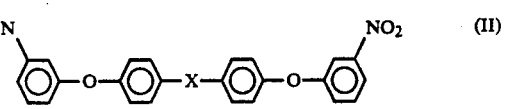

wherein X is a direct bond, divalent hydrocarbon having from 1 to 10 carbon atoms or a divalent group selected from $-C(CF_3)_2-$, $-CO-$, $-S-$, $-SO_2-$ or $-O-$ by a condensation reaction of a compound of formula (I)

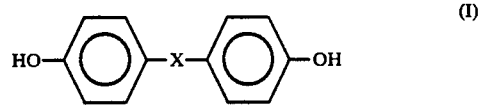

wherein X is defined above with m-dinitrobenzene comprising charging into a reaction vessel an aprotic polar solvent and a base which is an alkali metal carbonate, said base having a particle size that passes through a 60 mesh sieve, the amount of the base being from 1.0 to 1.5 moles per mole of the compound of formula (I), adding the compound of formula (I) an m-dinitrobenzene to the reaction vessel simultaneously with a constant feed ratio of from 2.0 to 2.1 moles of m-dinitrobenzene per mole of the compound of formula (I), and reacting the compound of formula (I) and the m-dinitrobenzene in the reaction vessel while removing water formed during the reaction.

2. The process of claim 1 wherein the compound of formula (I) and the m-dinitrobenzene are dropwise added to the reaction vessel.

* * * * *

UNITED STATES PATENT AND TRADEMARK OFFICE
CERTIFICATE OF CORRECTION

PATENT NO. : 5,296,635

DATED : March 22, 1994

INVENTOR(S) : KASE et al.

It is certified that error appears in the above-identified patent and that said Letters Patent is hereby corrected as shown below:

claim 1, column 12, line 37, after "(I)", "an" should be --and--.

Signed and Sealed this

Sixth Day of September, 1994

*Attest:*

BRUCE LEHMAN

*Attesting Officer*  *Commissioner of Patents and Trademarks*